United States Patent [19]
Barnea

[11] Patent Number: 6,117,075
[45] Date of Patent: Sep. 12, 2000

[54] DEPTH OF ANESTHESIA MONITOR

[75] Inventor: Ofer Barnea, Herzliyah, Israel

[73] Assignee: Meduck Ltd., Tel Aviv, Israel

[21] Appl. No.: 09/157,503

[22] Filed: Sep. 21, 1998

[51] Int. Cl.[7] .................................................... A61B 5/00
[52] U.S. Cl. ..................... 600/300; 600/485; 600/500; 600/549; 600/561
[58] Field of Search ...................... 600/300, 485, 600/490–6, 500–4, 544–7, 549, 561

[56] References Cited

U.S. PATENT DOCUMENTS

| | | | |
|---|---|---|---|
| 4,533,346 | 8/1985 | Cosgrove, Jr. et al. | 600/544 |
| 4,570,640 | 2/1986 | Barsa | 600/554 |
| 4,600,015 | 7/1986 | Evans et al. | 600/593 |
| 4,788,982 | 12/1988 | Gedeon et al. | 600/483 |
| 5,195,531 | 3/1993 | Bennett | 600/546 |
| 5,320,109 | 6/1994 | Chamoun et al. | 600/544 |
| 5,871,450 | 2/1999 | Nomura et al. | 600/500 |
| 5,891,050 | 4/1999 | Gensler et al. | 600/544 |
| 5,906,208 | 5/1999 | Ishikawa et al. | 600/300 |
| 5,913,826 | 6/1999 | Blank | 600/504 |

*Primary Examiner*—Robert L. Nasser
*Attorney, Agent, or Firm*—Mark M. Friedman

[57] ABSTRACT

A method and device for determining the depth of anesthesia. A pattern of very low frequency oscillations in measured skin temperature, or photoplethysmographic pulse pressure, is defined and analyzed. The frequency bandwidth of a frequency domain analysis of the oscillatory pattern, or the correlation between simultaneous oscillatory patterns measured at different physical locations, are used separately or fused to obtain an index of depth of anesthesia.

24 Claims, 5 Drawing Sheets

FIG. 3
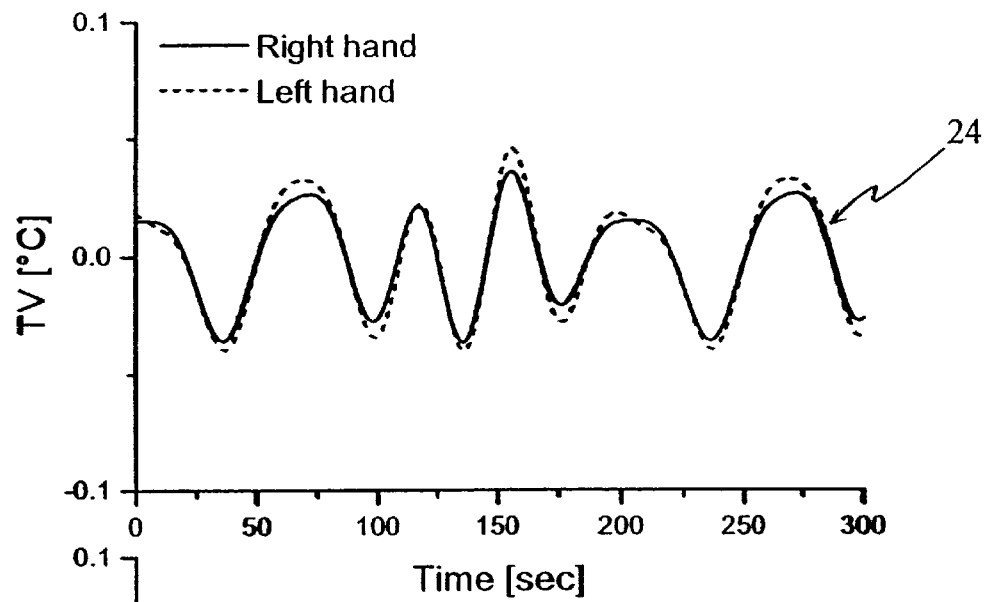
FIG. 3A
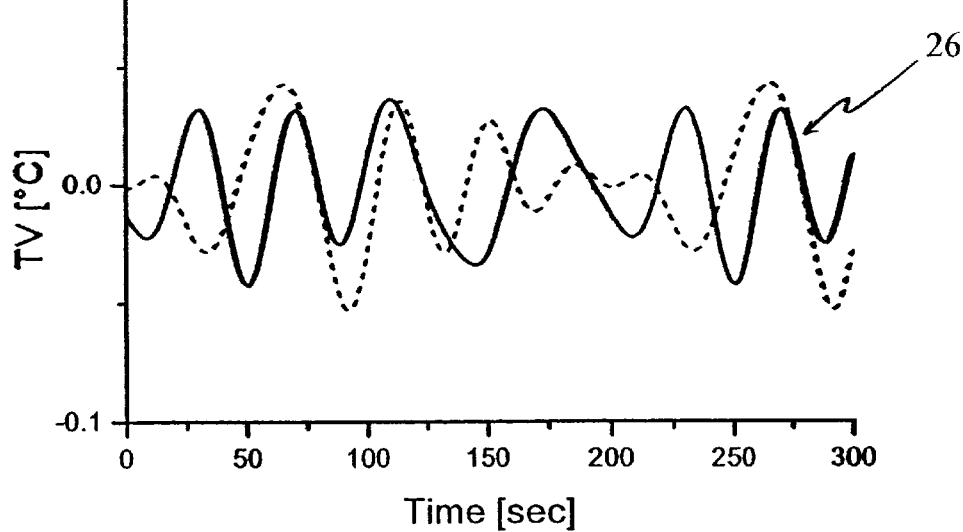
FIG. 3B

DEPTH OF ANESTHESIA MONITOR

FIELD AND BACKGROUND OF THE INVENTION

The present invention relates to medical monitoring methods and devices and, in particular, it concerns a method and device for monitoring the depth of anesthesia (DOA) during surgery.

It is known that monitoring of the depth of anesthesia during a surgical procedure is necessary so as to ensure both the comfort and safety of the patient, as well as a controlled surgical field for the surgeon. Current anesthetic practice is that the anesthesiologist infers the depth of anesthesia by observing several measured physiological variables, such as the patient's heart rate, systolic and diastolic blood pressure, and a photoplethysmographic (PPG) blood pressure waveform signal. Changes in these variables in response to surgical cuts or manipulations are interpreted by the anesthesiologist as indicating a level of anesthesia that is either adequate or inadequate. It is well known, however, that multiple factors, besides the DOA, may influence an individual patient's physiological response to a surgical stress, and that none of the above mentioned physiological variables, either singly or in combination, provide a truly objective indication of the DOA. As such, evaluation of the DOA by standard contemporary practice is an imprecise art, dependent on the knowledge and prior experience of the anesthesiologist. Furthermore, as the anesthesiologist is required to monitor and interpret the display readouts of several physiological variables simultaneously so as to evaluate the patient's DOA, the ongoing evaluation of the DOA, by standard contemporary practice, is a laborious procedure.

There has thus been much interest in developing sophisticated and automatic DOA monitors that could automatically and reliably monitor the DOA on an ongoing basis during a surgical procedure. To date, such devices have largely been based on the measurement of electrophysiological signals such as electrocardiographic (ECG) signals, electroencephalographic (EEG) signals, auditory and somatosensory evoked potentials, and craniofacial electromographic (EMG) signals. As all of the above biophysiological parameters involve measurable electric currents, they are hereinafter referred to as "electrically active" biological parameters, and are to be distinguished from those biological parameters which are not mediated by measurable electric currents, such as body temperature, blood pressure and other hemodynamic variables, which are hereinafter referred to as "electrically passive" biological parameters.

Analysis of electrically active parameters for the purpose of monitoring DOA has been found to be cumbersome and unreliable. Specifically, bispectral analysis of EEG signals (resulting in an index of anaesthetic depth known as the bispectral index), and other EEG-based parameters, have been shown to be unreliable predictors of DOA [Katoh T, Suzuki A, Ikeda K: Electroencephalographic Derivatives as a Tool for Predicting the Depth of Sedation and Anesthesia Induced by Sevoflurane. Anesthesiology 1998 Mar; 88 (3):642–650]. Furthermore, Thomsen et al. found that EEG based methods are particularly unreliable at deeper levels of anesthesia, when burst suppression patterns may occur on the EEG [Thomsen C E, Prior P: Quantitative EEG in Assessment of Anesthesia Depth. Methods of comparison. Ugeskr Laeger 1998 Feb 23;160 (9): 1323–1329].

A method for objectively and continuously determining the DOA of a patient during surgery would allow the anesthesiologist to administer the minimal dose of anesthetic required to achieve the desired DOA, thus minimizing anesthesia-related side effects. Furthermore, such a method would enable less experienced anesthesiologists to administer anesthesia in a more reliable and effective manner. There is therefore a need for, and it would be highly advantageous to have, a method for monitoring a patient's DOA, which is automatic, and not based on standard electrophysiological signal processing techniques.

SUMMARY OF THE INVENTION

The current invention is a method and device for monitoring DOA by analyzing patterns and characteristics of oscillatory phenomena in measured pulse pressure and skin temperature signals. The method is based on the fact that pulse pressure and skin temperature oscillatory patterns describe the nature of sympathetic vasomotor tone, changes in which parallel the depth of anesthesia. The method monitors DOA in two novel ways:

1. spectral characteristics of skin temperature or pulse pressure oscillatory phenomena are used to describe the depth of anesthesia, and
2. the concordance between oscillatory patterns of two physiological signals, which have been recorded simultaneously but at different locations, are used to describe the depth of anesthesia.

The invention may also be used to monitor the level of alertness of a subject in situations other than that of medical anesthesia, for example, to detect sleepiness and levels of relaxation in a subject who is driving a car, flying an airplane, operating heavy machinery, or carrying out any task requiring a high level of alertness. Hereinafter, the terms "depth of anesthesia", "level of sleepiness", and "level of relaxation" are jointly referred to as "levels of alertness".

According to the teachings of the present invention there is therefore provided a method for monitoring a level of alertness, including sensing an electrically passive oscillating biological parameter, generating a signal describing a pattern of oscillation of the parameter, quantifying at least one frequency domain parameter of the signal, and inferring a level of alertness from the at least one frequency domain parameter. There is also provided a method for monitoring a level of alertness of a subject, including synchronously sensing an oscillating biological parameter at at least two locations on the subject, generating at least two signals, each describing a pattern of oscillation of the parameter as sensed at one of the locations, calculating a descriptor of concordance between the signals, and inferring a level of alertness from the descriptor. There is also provided a system for monitoring a level of alertness, including a mechanism for sensing an electrically passive oscillating biological parameter, and a processor operative to generate a signal describing a pattern of oscillation of the parameter, and operative to quantify at least one frequency domain parameter of the signal. There is also provided a system for monitoring a level of alertness of a subject, including a mechanism for synchronously sensing an oscillating biological parameter at at least two locations on the subject, and a processor operative to calculate a degree of concordance between oscillatory patterns, as sensed at each of the locations, of the parameter.

BRIEF DESCRIPTION OF THE DRAWINGS

The invention is herein described, by way of example only, with reference to the accompanying drawings, wherein:

FIG. 3 is a set of graphs showing concordant and discordant temperature variation signals;

DESCRIPTION OF THE PREFERRED EMBODIMENTS

Figure 1:
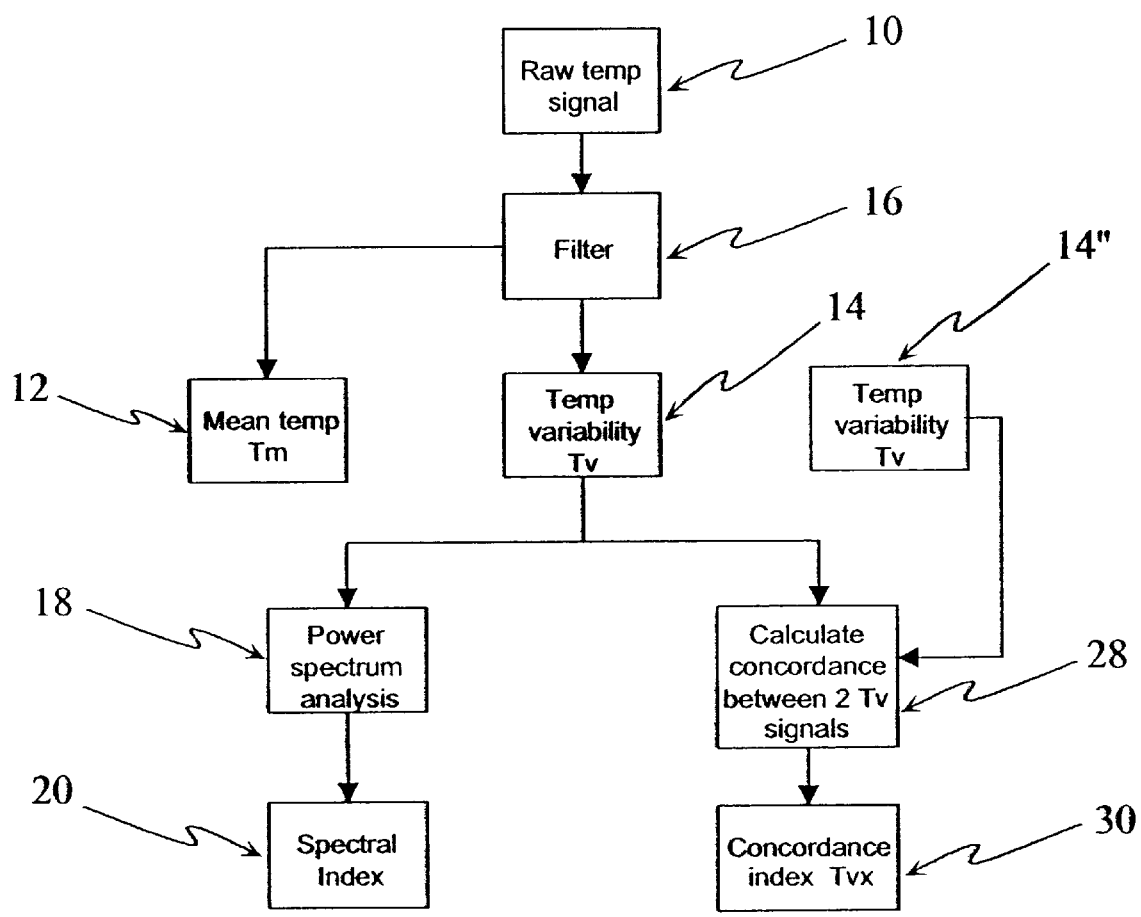
FIG. 1 is a schematic summary of a method for monitoring depth of anesthesia.

The present invention is a method and device for monitoring the depth of anesthesia.

The principles and operation of an anesthesia monitoring method and device, according to the present invention, may be better understood with reference to the drawings and the accompanying description.

Anesthetic agents influence the autonomic nervous system (that is, the sympathetic and parasympathetic nervous systems) by depressing brainstem sympathetic efferent activity. This results in hemodynamic changes reflective of decreased sympathetic tone, such as a decrease in heart rate and in myocardial contractility. In addition, as sympathetic tone is the major external determinant of smooth muscle activity in small arteries and arterioles [Seifert, H., K. Jager, and F. Bollinger: Analysis of flow motion by laser Doppler technique in patients with peripheral arterial occlusive disease. Clin Int J Microcirc Exp. 7:223–236, 1988], changes in sympathetic tone manifest as changes in pulse pressure (i.e. the difference between systolic and diastolic blood pressure) and changes in skin temperature (due to changes in the amount of blood flowing through peripheral capillaries). At the regional arteriolar level, sympathetic vasomotor tone is mediated via several control mechanisms concomitantly. Thus centrally mediated factors (such as the patients emotional state and state of relaxation, or the influence of anesthetic agents) and locally mediated factors (such as circulating catechloamine levels and local muscle activity) all influence the degree of vasoconstriction of peripheral arterioles. If higher (i.e. brainstem) mechanisms are disables, such as occurs under anesthesia, local mechanisms dominate the control of peripheral vasomotor tone.

It is well known that oscillatory behavior can be observed in electrophysiological phenomena such as heart rate variability and EEG alpha and beta wave activity. Study of heart rate oscillatory phenomena has shown that very low frequency oscillations (in the range of 0.01–0.04 Hz) in the R—R interval of the ECG are reflective of sympathetic effects. Parasympathetic effects, in contrast, manifest as high frequency oscillations (0.15–0.4 Hz). So too, vasomotor tone in any region of the body is never static, but rather oscillates under the constantly changing influences of sympathetic and other mediators, in a manner similar to that described above for the ECG R—R interval. The oscillatory behavior of peripheral vasomotor tone has been investigated by using noninvasive measurements of pulse-pressure amplitude and skin temperature as indices of smooth muscle tone. This research has revealed the existence of several waves of peripheral blood flow oscillations, each of a specific frequency [Colantuoni, A., S. Bergtulia, M. Intaglietta: Quantitation of rhythmic diameter changes in arterial microcirculation. Amer. J. Physiol. 246 (Heart Circ. Physiol. 15):H508–H517, 1984; and Fagrell, B: Microcirculatory methods for evaluating the effect of vasoactive drugs in clinical practice. Acta Pharm. Tox. 59:103–107, 1986]. In normal human subjects, Pagani has demonstrated respiratory-induced pulse pressure oscillations at a frequency of 0.2 Hz, and sympathetically mediated oscillations in pulse pressure at a frequency of 0.04 Hz [Pagani, M., O. Rimoldi, R. Furlan, and A. Malliani: Vascular Dynamics. Physiological Perspectives. Ed. N. Westerhof and D. R. Gross. New York and London: Plenum Press, 1988, 23–35]. So too, Shusterman et al have demonstrated the sensitivity of small skin-temperature oscillations to changes in subjects' sympathetic tone, by comparing conditions of deep relaxation with mental stress [Shusterman, V., K. Anderson and O. Barnea: Temperature Variability: Measurement and spectral analysis of skin temperature. Am J Physiol 273, R1173–R1181, 1997, which is incorporated herein by reference]. Furthermore, experimental neurophysiological studies indicate the presence of low frequency periodical patterns of sympathetic efferent discharge waves that remain active following blockage of low frequency blood pressure variability [Preiss, G., and C. Polosa: Patterns of sympathetic neuron activity associated with Mayer waves. Amer. J. Physiol. 226: 724–730, 1974].

Low frequency and high frequency oscillations reflective of sympathetic and parasympathetic influences, similar to those described above for heart rate, thus occur in non-electrophysiologic parameters, such as pulse pressure, as well. Skin temperature, too, manifests very low frequency oscillations, reflective of sympathetic effects, however high frequency oscillations are not measurable in skin temperature, as the physiological mechanisms for heat production and dissipation filter out such oscillations. Measurement of very low frequency pulse pressure and skin temperature oscillations can thus be utilized to monitor ongoing changes in a patient's sympathetic tone, and in an anesthetized patient such measurements can be interpreted to describe the depth of anesthesia.

Several embodiments of the method for monitoring DOA of the current invention are summarized schematically in FIG. 1, and will now be described in detail with reference to this figure.

In a first preferred embodiment of the present invention, the skin temperature of an anesthetized patient is continuously monitored. The recorded skin temperature signal, hereinafter referred to as the raw temperature signal 10, is then processed 16 so as to extract the following two data sets:

1. mean skin temperature over time ($T_M$) 12
2. very low frequency temperature variability over time ($T_V$) 14

These data sets are extracted 16 from raw temperature signal 10 by utilizing either a second order Butterworth bandpass filter or wavelet transformation at appropriate scales. $T_M$ 12 is obtained by extracting the trend, that is, the frequency components below 0.01 Hz alone, from the raw temperature signal, while $T_V$ is obtained by extracting the frequency components in the 0.01–0.04 Hz range. Alternatively, $T_M$ 12 can be obtained by subtracting $T_V$ 14 from raw temperature signal 10. As mentioned above, high frequency oscillations cannot be detected in skin temperature.

Spectral analysis is then performed 18 on $T_V$ 14 utilizing a power spectrum analysis method.

Figure 2:
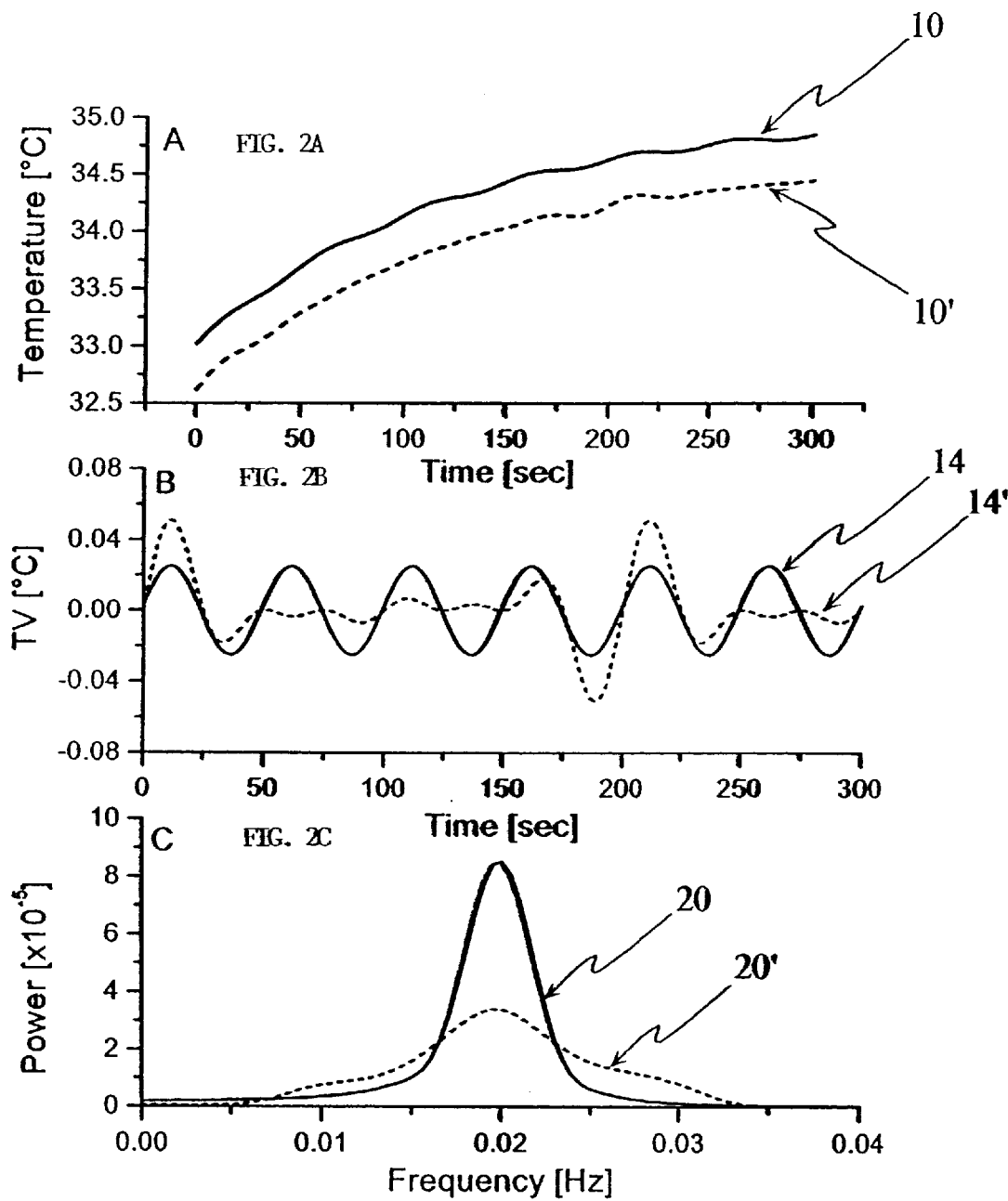
FIG. 2 is a set of graphs showing temperature recordings, very low frequency temperature variations, and power spectrum analyses of the temperature variations.

FIG. 2 demonstrates the techniques for analyzing skin temperature oscillations, as described above. Panel A in FIG. 2 shows two representative raw temperature signals 10 and 10' measured by temperature probes on the index fingers of two patients. The tracings show that in both patients the skin temperature gradually rises over time, and that in addition, small oscillations in skin temperature occur from second to second. Panel B shows $T_V$ signals 14 and 14' after they have been extracted from raw temperature signals 10 and 10' for each patient. Note that $T_V$ 14 approximates a sine wave, implying that a minimal number of sympathetic effectors are influencing the raw signal, while $T_V$ 14' is composed of several signals of differing frequencies and amplitudes, implying that multiple sympathetic control mechanisms are influencing the raw signal. This same phenomenon can be seen in Panel C, which shows the frequency power spectra 20 and 20' of the two $T_V$ signals 14 and 14'. Power spectrum 20 in panel C shows that the energy $T_V$ signal 14 is concentrated in a relatively narrow frequency band. In contrast, power spectrum 20' shows that the energy of $T_V$ signal 14' is spread over a larger frequency band. Note that even though both $T_V$ signals 14 and 14' have the same overall energy (i.e. the area under the curve), their frequency distributions are different. With increasing depth of anesthesia, higher (i.e. brainstem) sympathetic control of regional vasomotion is progressively abolished, leaving only local control mechanisms intact. Thus, as fewer mechanisms are involved in the control of local blood flow in states of anesthesia, the sympathetic activity signal is narrow-band.

In this embodiment of the current invention the frequency power spectrum characteristics of $T_V$ signal 14 are used to describe the DOA, such that a progressively narrower bandwidth describes a progressively deeper level of anesthesia.

FIG. 3 demonstrates a second preferred embodiment of the current invention. In this embodiment skin temperature is measured at paired identical locations (for example, the left and right thumbs or the left and right index fingers) simultaneously, on an anesthetized patient. The raw temperature signals are then processed as described above, so as to obtain two paired $T_V$ signals.

The two panels in FIG. 3 show two pairs 24 and 26 of synthesized signals simulating left and right hand $T_V$ signals. In the top panel the signals of pair 24 correlate well with each other, i.e. they increase and decrease in an harmonious manner, while the signals of pair 26 in the bottom panel demonstrate a poor correlation with each other. The relationship between the signals in each such pair can be determined using standard time domain or frequency domain methods, so as to give an index of the correlation (in the time domain) or the coherence (in the frequency domain) of the two signals. Hereinafter, the term "concordance" is used as a general term meaning both "correlation" and "coherence", depending on whether the time domain or the frequency domain, or both, are being referred to.

In the unanesthetized patient, brainstem sympathetic discharge effects each of the paired body locations equivalently, imposing a degree of oscillatory concordance on vasomotor tone at the two locations. However, with increasing depth of anesthesia, as higher sympathetic control of regional vasomotion progressively diminishes, local control mechanisms become dominant, and oscillatory concordance between distant locations is lost. In this embodiment of the current invention, the cross-correlation, or coherence, between two $T_V$ signals 22 and 14 is calculated 28 and then expressed as a concordance index ($T_{VX}$ 30). $T_{VX}$ 30 is used to describe the DOA, such that a progressively weaker $T_{VX}$ 30 describes a progressively deeper level of anesthesia.

Figure 4:
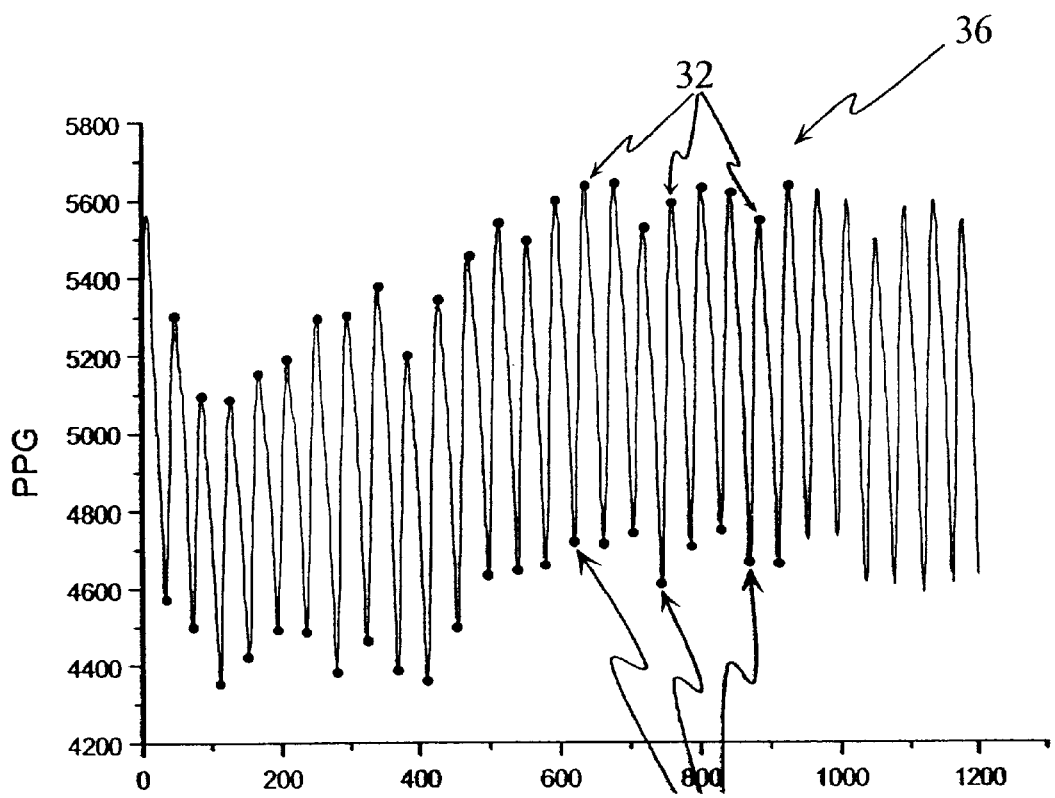
FIG. 4 is a typical photoplethysmographic signal.

In a third preferred embodiment of the current invention, a PPG signal of an anesthetized patient is continuously monitored. The recorded PPG signal, hereinafter referred to as the raw PPG signal, is then processed so as to generate a signal depicting the beat-to-beat pulse pressure amplitude ($PPG_A$). FIG. 4 shows a typical PPG signal 36. Positive peaks 32 and negative peaks 34 on PPG tracing 36 can be seen. The $PPG_A$ signal is derived by detecting peaks 32 and 34, and calculating the difference between each positive-negative peak pair. Thereafter, the $PPG_A$ signal is processed in a manner identical to that described above raw temperature signal 10, so as to derive a data set describing very low frequency variations in pulse pressure over time in the 0.01–0.04 Hz range, that is, the photoplethysmographic signal amplitude variability ($PPG_{AV}$). Power spectrum analysis is then performed on the $PPG_{AV}$ signal, as described above for the $T_V$ signal, and the $PPG_{AV}$ frequency power spectrum characteristics are used to describe the DOA, such that a progressively narrower bandwidth described a progressively deeper level of anesthesia.

In a fourth preferred embodiment of the current invention, PPG signals are measured at paired identical locations (for example, the left and right thumbs, the left and right index fingers, or the left and right earlobes) simultaneously, on an anesthetized patient. The raw PPG signals are then processed as described above, so as to obtain two paired $PPG_{AV}$ signals. In a similar manner to that described for $T_V$ signal pairs 24 and 26, the correlation or coherence between the time-widowed $PPG_{AV}$ signals in both hands ($PPG_{AX}$) is calculated and used to describe the DOA, such that a progressively weaker $PPG_{AX}$ describes a progressively deeper level of anesthesia.

Although the method for monitoring DOA of the current invention has been described with regard to indices of temperature and pulse pressure oscillatory behavior individually, it will be understood that two or more of the above described indices may be combined, using data-fusion or other methods, so as to generate additional indices of DOA. It will also be understood that the method of the current invention may be applied to many hemodynamic parameters, such as heart rate, systolic blood pressure, diastolic blood pressure, mean blood pressure, cardiac output, systemic resistance, and others. Furthermore, analysis of other physiological oscillatory phenomena, such as the relationship between oscillations of different frequencies, higher frequency $PPG_A$ oscillations (in the 0.04–0.15 Hz or 0.15–0.4 Hz ranges), or power spectrum energy characteristics, may be utilized to describe DOA, without departing from the spirit of the current invention. In addition, signal measurements made at two or more locations that are not necessarily paired may also be analyzed as described herein, so as to describe DOA.

Figure 5:
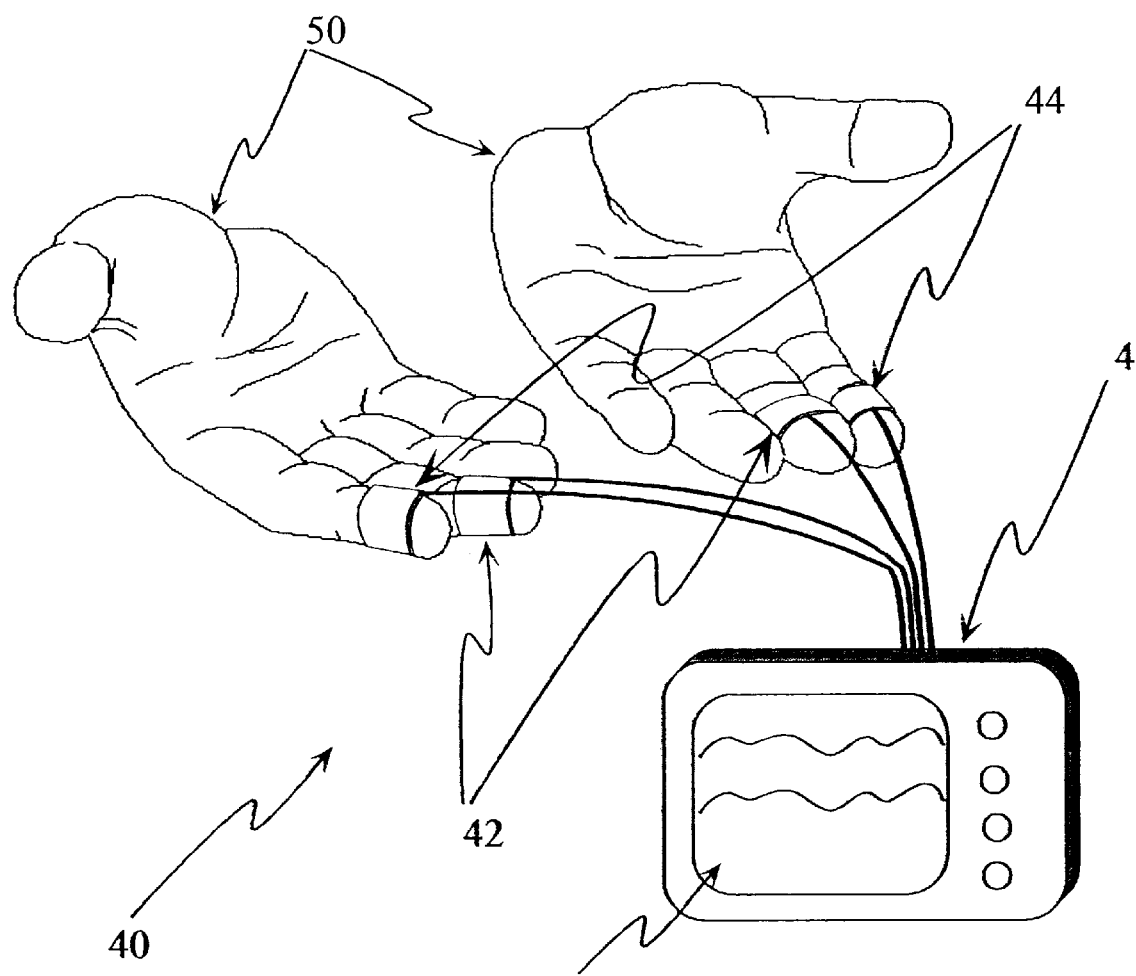
FIG. 5 is a schematic diagram of a device suitable for monitoring depth of anesthesia in accordance with the method of the present invention.

FIG. 5 shows a preferred embodiment of a device 40 suitable for monitoring the depth of anesthesia in accordance with the method of the present invention.

On each hand of a patient 50, two transducers are attached to the fingers: a high resolution temperature probe 42 and a photoplethysmograph (PPG) 44.

Temperature probes 42 comprises a 14 bit analog to digital (A/D) converter, a 10 K $\Omega$ at 25° C. thermistor such as a BR32 (Thermometrics, NJ), and a 10K $\Omega$ resistor. The latter two are connected in a voltage divider using a reference voltage source of 2.5V. The voltage on the thermistor (0.8–1.25V in the range of 25–40° C.) is amplified and shifted so as to obtain a full-scale voltage of 0–5V for the temperature range of 25–40° C. The 14 bit A/D converter maintains a sensitivity of approximately 0.8–1.035 thousands of a degree over this temperature range. When configured in this manner, temperature probe 42 has very high resolution (0.001° C.) and accuracy of ±0.1° C.

PPG 44 comprises a standard photoplethysmograph, for example a Single Patient SatSensor (Datex-Ohmeda Division, Instrumentarium Corp., Helsinki, Finland). PPG 44 measures blood volume in the finger tip, a measurement that accurately reflects the blood pressure waveform. The PPG signal can be calibrated to the patient's blood pressure as measured by standard noninvasive blood-pressure measurement methods.

PPG 44 and temperature probe 42 are connected to a computer processor 46. Computer processor 46 performs the signal processing calculations described above on the signal inputs received from temperature probes 42 and PPGs 44, using standard signal processing and image processing software algorithms. The signals input to computer processor 46, as well as the results of the signal processing calculations described above, are displayed on a display 48. Other physiological parameters monitored during the course of surgery may also be processed by computer processor 46 and displayed on display 48. Thus device 40 may combine measurements of ECG, two channels of EEG, PPG on two hands, and skin temperature on two hands.

There has therefore been described a method and device for monitoring the depth of anesthesia, or level of alertness, automatically and continuously, without the direct use of electrophysiological signals. The method utilizes physiological parameters that are easily routinely measured with standard anesthetic monitoring equipment, and provides a reliable, accurate, and easily understandable depiction of the depth of anesthesia.

What is claimed is:

1. A method for monitoring a level of alertness, comprising
   a) sensing an electrically passive oscillating biological parameter;
   b) generating a power-frequency distribution describing a pattern of oscillation of said parameter;
   c) quantifying a frequency axis dimension of a peak frequency bandwidth of said power-frequency distribution; and
   d) inferring a level of alertness from said quantified frequency axis dimension.

2. The method of claim 1, wherein said electrically passive oscillating biological parameter includes a pulse pressure.

3. The method of claim 1, wherein said pattern of oscillation is of a frequency within the range of 0.01 to 0.4 Hz.

4. The method of claim 1, wherein said signal is generated by a technique of wavelet transformation.

5. The method of claim 1, wherein said inferred level of alertness is a depth of anesthesia.

6. A method for monitoring a level of alertness of a subject, comprising
   a) synchronously sensing an oscillating biological parameter at at least two locations on the subject, wherein said locations are paired body parts;
   b) generating at least two signals, each describing a pattern of oscillation of said parameter as sensed at one of said locations;
   c) calculating a descriptor of concordance between said signals; and
   d) inferring a level of alertness from said descriptor.

7. The method of claim 6, wherein said parameter is selected from the group consisting of skin temperature and pulse pressure.

8. The method of claim 6, wherein said pattern of oscillation is of a frequency within the range of 0.01 to 0.4 Hz.

9. The method of claim 6, wherein said signals are generated by a technique of wavelet transformation.

10. The method of claim 6, wherein said concordance between said signals is selected from the group consisting of a correlation in the time domain and a coherence in the frequency domain.

11. The method of claim 6, wherein said inferred level of alertness is a depth of anesthesia.

12. A system for monitoring a level of alertness, comprising
    a) a mechanism for sensing an electrically passive oscillating biological parameter; and
    b) a processor operative to generate a power-frequency distribution describing a pattern of oscillation of said parameter, and operative to quantify at least one frequency axis dimension of a peak frequency bandwidth of said power-frequency distribution.

13. The system of claim 12, wherein said mechanism is selected from the group consisting of photoplethysmographs and temperature probes.

14. The system of claim 12, wherein said electrically passive oscillating biological parameter is selected from the group consisting of skin temperature and pulse pressure.

15. A system for monitoring a level of alertness of a subject, comprising
    a) a mechanism for synchronously sensing an oscillating biological parameter at two paired locations on the subject; and
    b) a processor operative to calculate a degree of concordance between oscillatory patterns, as sensed at each of said paired locations, of said parameter.

16. The system of claim 15, wherein said mechanism is selected from the group consisting of photoplethysmographs and temperature probes.

17. The system of claim 15, wherein said parameter is selected from the group consisting of skin temperature and pulse pressure.

18. A method for monitoring a level of alertness, comprising
    a) sensing a skin temperature;
    b) generating a signal describing a pattern of oscillation of said sensed skin temperature;
    c) quantifying at least one frequency domain parameter of said signal; and
    d) inferring a level of alertness from said at least one frequency domain parameter.

19. The method of claim 18, wherein said pattern of oscillation is of a frequency within the range of 0.01 to 0.4 Hz.

20. The method of claim 18, wherein said signal is generated by a technique of wavelet transformation.

21. The method of claim 18, wherein said at least one frequency domain parameter is quantified by a power spectrum analysis technique.

22. The method of claim 18, wherein said inferred level of alertness is a depth of anesthesia.

23. The method of claim 18, wherein said level of alertness is inferred from a dimension of a frequency bandwidth of said at least one frequency domain parameter.

24. A system for monitoring a level of alertness, comprising
    a) a temperature probe for sensing a skin temperature; and
    b) a processor operative to generate a signal describing a pattern of oscillation of said sensed skin temperature, and further operative to quantify at least one frequency domain parameter of said signal.

* * * * *